United States Patent [19]

Mendiratta

[11] 4,391,997
[45] Jul. 5, 1983

[54] ION EXCHANGE CATALYZED BISPHENOL PROCESS

[75] Inventor: Ashok K. Mendiratta, Schenectady, N.Y.

[73] Assignee: General Electric Company, Schenectady, N.Y.

[21] Appl. No.: 314,164

[22] Filed: Oct. 23, 1981

[51] Int. Cl.³ .................... C07C 37/20; C07C 39/16
[52] U.S. Cl. ................................. 568/727; 568/722; 568/723; 568/728
[58] Field of Search ................ 568/727, 728, 722, 723

[56] References Cited

U.S. PATENT DOCUMENTS

| 2,775,620 | 12/1956 | Williamson | 568/727 |
| 3,049,569 | 8/1962 | Apel et al. | 568/727 |
| 3,221,061 | 11/1965 | Grover et al. | 568/728 |
| 4,051,079 | 9/1977 | Melby | 210/30 |
| 4,191,843 | 3/1980 | Kwantes et al. | 568/727 |
| 4,277,628 | 7/1981 | Granahan | 568/749 |
| 4,301,305 | 11/1981 | Keidik et al. | 568/727 |
| 4,308,404 | 12/1981 | Kwantes et al. | 568/727 |

FOREIGN PATENT DOCUMENTS 148515  5/1981  Fed. Rep. of Germany ...... 568/727

*Primary Examiner*—Werren B. Lone
*Attorney, Agent, or Firm*—Richard J. Traverso; James C. Davis, Jr.; James Magee

[57] ABSTRACT

An ion exchange catalyzed bisphenol process is described wherein condensation reaction temperature is increased along the path of the reaction which limits the formation of color bodies, tars and other condensation reaction by-product impurities.

9 Claims, 1 Drawing Figure

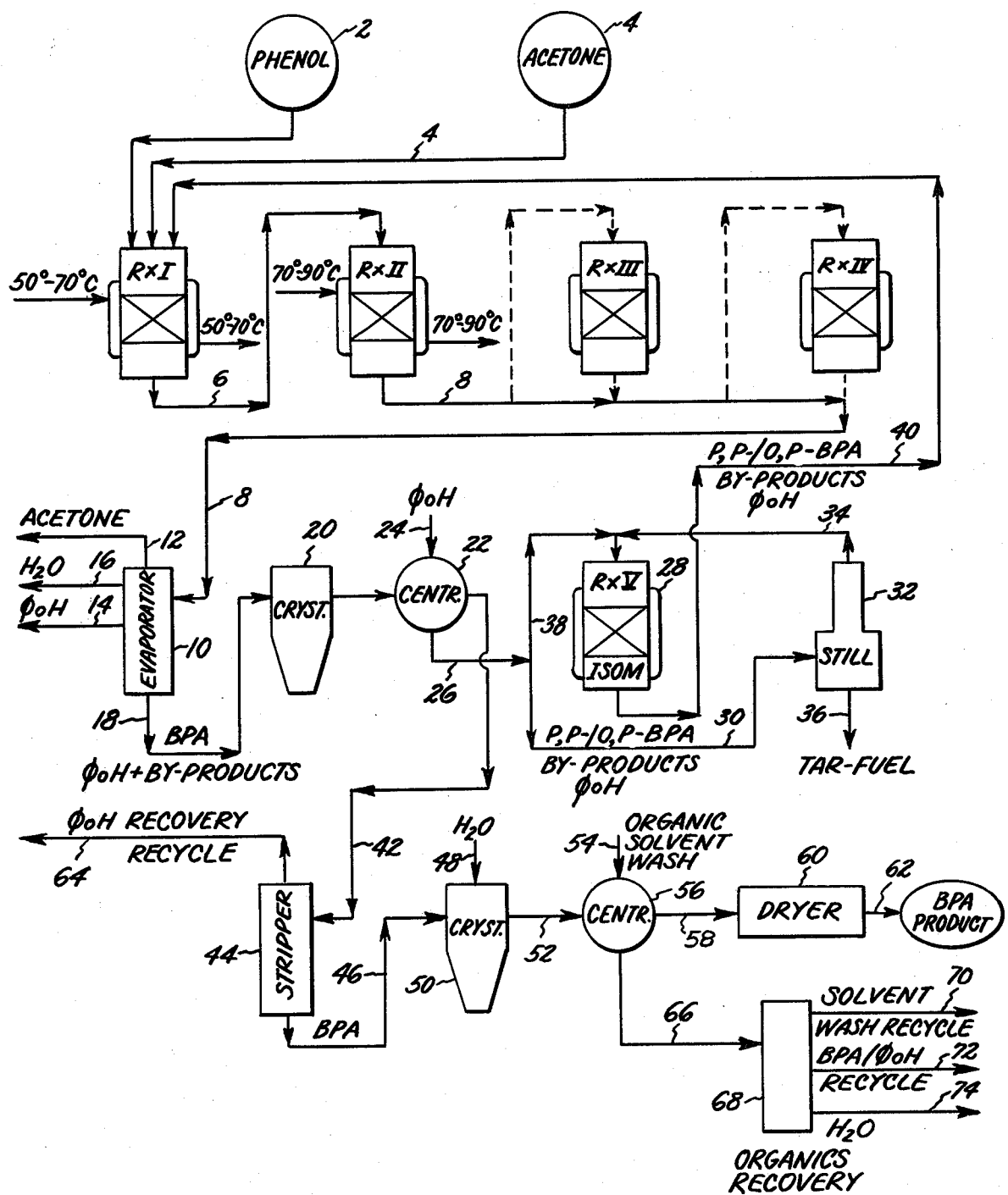

ION EXCHANGE CATALYZED BISPHENOL PROCESS

This invention relates to an ion exchange catalyzed process for making bisphenols. More particularly, the present invention relates to such a process with condensation reaction temperature increasing along the path of the reaction whereby limited quantities of color bodies, tars and other condensation reaction by-product impurities are formed.

U.S. Pat. No. 2,775,620 - Williamson describes a process whereby condensation of phenol and acetone to produce bisphenol-A is carried out under homogeneous condensation reaction conditions employing strong mineral acids in a series of reactors wherein all of the acid catalysts and all of the phenol is charged to the first reactor along with a portion of the acetone employed in the process with subsequent quantities of acetone being introduced into the following reactors, resulting in a purer final reactor bisphenol-A product.

U.S. Pat. No. 3,049,569 - Apel et al. describes preparation of ultra-high purity bisphenol-A employing a heterogeneous specific ion-exchange resin modified by mercapto alcohol wherein the reactor effluent is separated from BPA into streams containing reaction by-products, acetone and phenol which are recycled along with fresh feed to the reactor in order to minimize the formation of by-products under steady state reaction conditions.

U.S. Pat. No. 3,221,061 - Grover et al. describes an improvement over the Apel et al. process by passing the by-product stream through a rearrangement isomerization process step wherein the by-product stream is rearranged in a series of reactors maintained in descending temperature profile in order to effect a reduced equilibrium concentration of by-products in the process under steady state process conditions.

U.S. Pat. No. 4,051,079 - Melby describes the reactivation of acidic ion exchange resins used in the condensation of phenol and acetone in the preparation of bisphenol-A in order to remove metals and by-product tars such as isoprophenylphenol, isopropenylphenol dimer, and oligomers, Dianin's compound, spiroindane bisphenol, and a complex mixture of other compositions including trisphenols, and higher polyphenols. Catalyst regeneration is carried out by employing a phenol-water solution containing an acid having a pKa of less than about 3.

In brief, the prior art recognizes that in the preparation of bisphenol-A via the condensation reaction of phenol with acetone in the presence of either a homogeneous or heterogeneous catalyst the formation of undesirable by-products effects the material losses and ultimate color and purity of bisphenol-A and that many options have been employed in the processes described in order to minimize the formation of color bodies, tars, and other undesirable reaction product impurities.

Unexpectedly, this invention describes a process for the preparation of bisphenol-A carried out under kinetic reaction condition such that phenol and acetone are converted to bisphenol-A in the presence of an ion-exchange resin in a series of reactors having an ascending temperature profile whereby high purity bisphenol-A is prepared in the substantial absence of undesirable by-product color bodies, tars and other reaction product impurities.

The process of this invention is carried out in a reactor or series of reactors having an ascending temperature profile along the reaction path under kinetic reaction conditions wherein para,para-bisphenol-A is prepared on a mole ratio basis in amounts of at least 92% and often amounts as great as 96% relative to the ortho,para-bisphenol-A formed in conjunction with the well known color bodies, tars and other reaction by-product impurities associated with bisphenol-A condensation reaction conditions.

The process of this invention, because of a reduction in amount of by-product impurities and color formed in the reactor, (1) reduces the amount of by-product impurities which, after separation from the crude-bisphenol-A are recycled, for isomerization in the presence of excess phenol and returned to the reaction zones as a portion of the feed stock as well as;

(2) reduces the amount of by-product impurities necessarily cracked in a phenol recovery waste process stream carried out in accordance with the teachings of Carnahan in U.S. Pat. No. 4,277,628 and hence reduces the material losses in the system.

The process of the present invention can therefore, result in improved reactor effluent product disribution and color, thus yielding high material usage and improved BPA product or color.

Advantageously, the process of this invention describes operating parameters which can be widely varied and which permit the steady state conversion of phenol and acetone to bisphenol-A under highly desirable reaction conditions which minimize capital and operating costs commonly associated with many of the processes described in the prior art.

A typical embodiment of the present process for the preparation of bisphenol-A comprises reacting phenol and acetone in the presence of a cation exchange resin in a continuous reactor system with reaction temperature increasing along the reactor or alternatively in a series of reactors operated at progressively increasing temperatures. More particularly there is provided a process for the production of bisphenol-A comprising reacting phenol and acetone in the presence of a cation-exchange resin in a continuous reactor system with reaction temperature increasing along the reactor or alternatively in a series of reactors operated at progressively increasing temperatures to produce a mixture of bisphenol-A, phenol, acetone, water and phenolacetone condensation by-products. The reactor effluent may then be treated by any conventional means to separate the bisphenol-A from the by-products and also from the reactants so that they may be recycled, for example, separating a mixutre of bisphenol-A and by-products from the phenol, acetone and water by evaporation/distillation; separating the water from the phenol and acetone by distillation/evaporation; returning substantially anhydrous phenol and acetone to the bisphenol-A reactor system; crystallizing the bisphenol-A in the presence of phenol to produce solid bisphenol-A-phenol adduct and a mother liquor containing phenol-bisphenol-A, and condensation by-products; cracking a minor portion of the mother liquor to form phenol and cracking products; isomerizing a major portion of the mother liquor in the presence of an ion-exchange resin; recycling the isomerization products as well as the phenol from the cracking operation to the first bisphenol-A reactor to provide at least a portion of the feedstock; removing phenol from the solid BPA-phenol adduct by evaporation; crystallizing the crude BPA in the presence of water to yield BPA crystals; washing the BPA crystals with a suitable organic solvent to yield pure BPA product free of any impurities and color bodies.

The present process for conducting the condensation of phenol and acetone to form bisphenol-A can be carried out in accordance with those well established in the art. Mole ratios of phenol and acetone can be from about 2:1 to about 10:1 and as high as about 30:1. Substantially anhydrous reaction conditions can be used whereby the by-product condensation reaction water content of the process is less than 2% and preferably less than 1.5%. Substantially anhydrous acetone or anhydrous recycle isomerization or cracked condensation products.

The reaction can be carried out at between about 50° C. and about 120° C. preferably about 60° C. and 80° C.

The weight hourly space velocity (WHSV) of the reactor feed to the first reactor and the effluent streams subsequently passed to the down stream reactors may vary within the limits of from about 0.05 to about 15 parts by weight of feed stream per part by weight of catalyst per hour. Based on the weight hourly space velocity of the feedstock under steady state reaction conditions. The conversion of acetone can vary widely from as little as about 20% to about 82%.

Conventional ion-exchange resin catalysts can be used, e.g. strong-acid ion exchange resins, including resins or polymers having a plurality of appended sulfonic acid groups. Examples include sulfonated polystyrene or poly(styrene-divinyl-benzene) copolymers and sulfonated phenol-formaldehyde resins. Specific examples of commercially available resins are; Amberlite ® or Amberlyst ® manufactured by Rohm and Haas, Dowex ® manufactured by Dow Chemical Company, Permutit QH ® manufactured by Permutit Company, Chempro C-20 ® manufactured by Chemical Process Company. As stated before, the acidic ion exchange groups with mercapto alkyl amines, by partially esterifying the acid resins with a mercapto alcohol, or with an alkyl amine precursor such as thiazolidines. The unmodified ion-exchange resins generally have an ion-exchange capacity preferably of at least about 2.0 milliequivalents H+, with exchange capacities in the range of from about 3 to about 4 milliequivalents of H+ per gram of dry resin. About 5% to about 35% of acid sites are modified by reacting the acid sites with a mercapto group.

The term bisphenol-A or BPA refers to the commercially important 2,2′-bis(4-hydroxyphenyl)propane. As will be apparent to those of ordinary skill in the art, the process of the preparation of bis(hydroxyphenyl)compounds and such compounds are derived by substituting or including, in addition to the reactant phenol (i.e. also known as monohydroxybenzene), other phenolic type reactants including ortho- and meta-cresol; 2,6-dimethyl phenol; ortho-secondary butylphenyl; ortho-tertiary butylphenol; 2,6-ditertiary butylphenol; 1,3,5-xylenol, tetramethylphenol; 2-methyl-6-tertiary-butyl-phenyl; ortho-phenyl-phenol; ortho-meta-chloro-phenol; ortho-bromophenol; t-chloro-ortho-cresol; 2,6-dichlorophenol. Monohydroxybenzene is obviously the preferred phenolic reactant because of the commercial importance of bisphenol-A.

In addition to acetone, otherwise known as dimethyl ketone, the process of this invention can be carried out by substituting aldehydes or other ketones for acetone. Specific examples include methyl ethyl ketone, methyl propyl ketone, acetophenone, methyl vinyl ketone, cyclopentanone, cyclohexanone, benzophenone, hexalfluoroacetone, etc. Again because of the commercial significance of bisphenol-A, acetone is the preferred reactant.

The drawing is a schematic flow diagram illustrating one example of the process of the present invention. All proportions in the description which follows are on a weight percent basis unless otherwise specified.

Phenol from phenol reservoir 2, acetone from reservoir 4, and recycle phenol/p,p-bisphenol-A/o,p-bisphenol-A plus steady state reaction by-products from the ion-exchange isomerizer 28 are charged to ion-exchange BPA reactor RxI heated to a temperature of about 50° C. to about 70° C. The effluent from the reactor is passed to a second ion exchange reactor RxII heated to a temperature of about 70° C. to 90° C. Effluent from the first reactor is passed to a second reactor RxII then optionally to subsequent reactors with an increasing overall temperature profile. The effluent condensation product stream 8 of bisphenol-A from the ion exchange reactor RxII containing bisphenol-A, unreacted phenol and acetone, water, color bodies, tars and other reaction by-product impurities is passed to acetone/water/phenol evaporator unit 10. The acetone/phenol/water mixture is stripped of water and the anhydrous acetone stream 12 and phenol stream 14 are recycled to the BPA reactor RxI. Waste water stream 16 is purged. Bottom product stream 18 containing crude bisphenol-A, phenol, color bodies, tars and other by-products is crystallized to yield a 1:1 molar adduct complex of phenol and bisphenol-A in crystallizer 20. The mother liquor and 1:1 adduct are separated in centrifuge 22. A phenol wash 24 is given to the adduct crystals in the centrifuge 22. The mother/wash liquor stream 26 containing typically 70–85% phenol, 5 to 15%, p,p-bisphenol-A and the balance being color bodies, tars and by-products is passed to an ion-exchange isomerization reactor 28 for isomerization of a portion of the by-products to p,p-bisphenol A. A portion of stream 26 is passed via stream 30 to the cracking still 32 and cracked to yield phenol, stream 34, and tar-fuel, stream 36, at a temperature of from 150°–300° C. in the presence of a suspended aluminum alkoxide cracking catalyst. The overhead phenol stream 34 from the cracking distillation unit is combined with the balance mother/wash liquor stream 38 from the adduct crystallization step. This combined stream is passed through the ion-exchange isomerization reactor 28 for rearrangement of condensation reaction products to p,p-bisphenol-A. The product of the isomerizar RxV is recycled to RxI via stream 40. Residual tars stream 36 is ultimately disposed of. Crude bisphenol-A after separation as a 1:1 molar BPA/phenol crystalline adduct is removed from centrifuge 22 via stream 42. Phenol is removed from the adduct of the stripper 44. The overhead phenol stream 64 is recycled back to the reactor system.

Pure bisphenol-A is crystallized in crystallizer 50 from crude bisphenol-A stream 46 in the presence of water from stream 48. The crystals are separated from the slurry stream 52 in centrifuge 56. An organic solvent wash is given to the crystals to remove the surface impurities. High purity bisphenol-A product crystals 58 are dried in drier 60 and packaged 62 for use in the preparation polycarbonate and/or other polymers. The mother/wash liquors stream 66 from the centrifuge 56 is sent to the organics recovery unit 68 for recovery of the organic solvent 70, bisphenol-A/phenol stream 72 with residual impurities and color bodies and aqueous stream 74, which are recycled to the organic solvent wash 54, adduct crystallizer 20 and the aqueous crystallizer 50, respectively.

The following specific examples illustrate the process of this invention.

EXAMPLES

Three 25 mm diameter tubular glass reactors were connected in series. Isothermal operation was maintained in each reactor by circulating hot oil through the reactor jacket. The catalyst used in all three reactors was microreticular sulfonated polystyrene divinyl benzene ion-exchange resin (Amberlite-118 ®) with about 10% of its acid sites neutralized with 2-mercapto-ethylamine. The catalyst loading in each reactor was 25 grams dry weight basis and had a mesh size range from 28–48. Under steady state reaction conditions a phenol-/acetone feedstock mixture having a phenol: acetone mole ratio of 10:7:1 was passed into the first reactor. Bisphenol-A reaction product effluent from the first reactor was passed as feedstock to the second reactor of the series. Bisphenol-A reaction product from the second reactor was then passed as feedstock to the third reactor of the series. Effluent from the third reactor was collected for characterization.

High pressure liquid chromatography and ultraviolet spectroscopy were used for reactor effluent component analysis and color analysis, respectively. The color of the reaction mixture was measured by finding the absorbance value of a 10% sample solution in methanol (i.e., 5 gm sample diluted with 50 ml methanol) at 350 nm wavelength and 10 cm path-length in a Varian Cary 219 spectrophotometer. The feedstock steady state flow for control purposes was 8.3 mls. per minute equivalent to a weight hourly space velocity (WHSV) of 7.30 gms feed/hr/gm of catalyst. The temperature profile of the reactors series was varied as set out in Table I. The product/by-product of the condensation reactions under the inventive and control (contrasting) reactions conditions are set out in Table I. Acetone conversion in the example remained constant at about 69%. The results described therein illustrates that using constant or descending temperature reactor profiles, the amount of color bodies, tars and other reaction by-product impurities produced are increased whereas unexpectedly the ascending reaction temperature profile of this invention decreases the occurrence of by-products deleterious to the commercial use of bisphenol-A in the manufacture of high molecular weight polycarbonate. In example 5, the amount of deleterious by-products increased due to the high final reactor temperatures, 90° C.

least 98+ to 99+ percent, while by-products, deleterious to the color, oxidation and thermal stability of the ultimate polycarbonate end product are significantly limited in amounts.

While the invention is described with respect to a particularly preferred embodiment, it will be apparent to those of ordinary skill in the art that certain modifications and changes may be made without departing from the spirit instilled in the invention and therefore it is intended that certain modifications and changes may be made without departing from the spirit instilled in the invention and that the foregoing disclosure be limited only to the claims appended hereto.

What is claimed is:

1. A process for the preparation of bisphenol-A comprising reacting phenol and acetone in the presence of a cation exchange resin catalyst in a continuous reactor system with reaction temperature increasing along the reactor or alternatively in a series of reactors operating at progressively increasing temperatures.

2. The process of claim 1 wherein the phenol to acetone ratio is between about 3 to 1 and about 20 to 1 by weight.

3. The process of claim 1 wherein the catalyst is a 2-mercapto-ethyl amine modified microreticular sulfonated polystyrene divinyl benzene ion-exchange resin.

4. The process of claim 1 wherein the catalyst is a sulfonated polystyrene divinyl benzene ion-exchange resin.

5. The process of claim 1 wherein the weight hourly space velocity through the reactor is between about 0.05 to about 15 parts by weight of feedstream per part by weight of catalyst per hour.

6. The process of claim 1 wherein the reaction temperature is between about 45° C. and about 120° C.

7. The process of claim 1 wherein the reaction temperature is between about 60° C. and about 90° C.

8. The process for the production of bis(hydroxyphenyl) alkanes comprising reacting a phenolic compound, having at least one replacable hydrogen atom attached directly to a carbon atom in a phenolic ring, with an aliphatic ketone in the presence of a cation exchange resin in a continuous reactor system with reaction temperature increasing along the reactor length or alternatively in a series of reactors operating at progressively increasing temperatures.

9. The process for the preparation of 2,2-di(hydroxyphenyl)propane comprising reacting phenol and acetone in tthe presence of a 2-mercapto-ethyl amine modified microreticular sulfonated polystyrene divinyl benzene ion-exchange resin at a temperature of between about 60° C. and about 80° C. in a continuous reactor system with reaction temperature increasing along the

TABLE I

| | EFFLUENT PRODUCT DISTRIBUTION OF 3rd REACTION | | | | | | |
|---|---|---|---|---|---|---|---|
| | Temperature °C. | | | Product Distribution wt % | | | Δ COLOR (ABSORBENCE EFFLUENT- |
| EXAMPLE | 1st Rx | 2nd Rx | 3rd Rx | p,p-BPA | o,p-BPA | Others* | ABOSRBENCE FEED) |
| 1 | 70 | 70 | 70 | 95.17 | 3.73 | 1.1 | 0.0850 |
| 2 | 80 | 70 | 60 | 94.09 | 4.56 | 1.35 | — |
| 3 | 60 | 70 | 80 | 95.40 | 3.80 | 0.80 | 0.0700 |
| 4 | 60 | 80 | 80 | 94.91 | 4.17 | 0.92 | — |
| 5 | 60 | 70 | 90 | 94.53 | 4.23 | 1.24 | — |

*The remainder consists of typical condensation by-products, e.g., BPXI, BPXII, spirobiinane, IPP dimers, chromanes, etc.

As illustrated by Examples 1–5 under steady state reaction conditions, p,p-bisphenol-A is formed in yields of at least about 94+ percent p,p-bisphenol-A plug o,p-bisphenol-A are formed in combined yields of at reactor or alternatively in a series of reactors operating at progressively increasing temperatures.

* * * * *